United States Patent [19]

Frisch

[11] Patent Number: 4,908,031
[45] Date of Patent: Mar. 13, 1990

[54] TOE IMPLANT

[75] Inventor: Eldon E. Frisch, Midland, MI.

[73] Assignee: Dow Corning Wright, Arlington, Tenn.

[21] Appl. No.: 385,619

[22] Filed: Jul. 27, 1989

[51] Int. Cl.⁴ .............................................. A61F 2/42
[52] U.S. Cl. ........................................ 623/21; 623/16
[58] Field of Search ....................... 623/21, 20, 18, 16

[56] References Cited

U.S. PATENT DOCUMENTS

| | | | |
|---|---|---|---|
| 3,462,765 | 8/1969 | Swanson | 623/21 |
| 3,875,594 | 8/1973 | Swanson | 623/21 |
| 3,918,101 | 11/1975 | Lagrange et al. | 623/20 |
| 4,156,296 | 5/1979 | Johnson et al. | 623/21 |
| 4,158,893 | 10/1976 | Swanson | 623/21 |
| 4,198,713 | 3/1979 | Swanson | 623/21 |
| 4,231,121 | 7/1979 | Lewis | 623/21 |
| 4,242,759 | 3/1979 | White | 623/21 |
| 4,304,011 | 8/1980 | Whelan, III | 623/21 |
| 4,642,122 | 4/1986 | Steffee | 623/21 |
| 4,685,919 | 3/1986 | Niwa et al. | 623/21 |
| 4,790,851 | 12/1988 | Suire et al. | 623/16 |

Primary Examiner—Ronald L. Frinks
Attorney, Agent, or Firm—Allan O. Maki

[57] ABSTRACT

The invention provides an improved prosthetic toe joint adapted for replacement of a human toe joint which includes at least one one-piece member for implantation into the bone of the joint. The implant has a concave articulating surface which articulates against another one-piece component having a mating convex surface or against a mating convex bone surface. This one part component is provided with a flexible hinge section at the junction of its stem and the enlarged head portions. The hinge section is formed from a section of the stem which extends laterally outwardly on both sides of the stem portion adjacent the junction with the head. The laterally enlarged section is provided with a longitudinal channel extending through its midsection to form a hinge. Each of the one-piece components is preferably molded of a flexible elastomeric, physiologically inert material, for example medical grade silicone rubber.

4 Claims, 1 Drawing Sheet

TOE IMPLANT

FIELD OF THE INVENTION

This invention relates to a prosthetic device for replacement of a joint in a human being, and, more specifically, to an improved implantable toe joint.

BACKGROUND OF THE INVENTION

Various prostheses have been developed for replacing joints in human bodies, including joints for the toes and fingers. Many of these prostheses are formed of elastomeric polymeric material in one piece with a hinge section positioned in the joint area. Example of such prostheses are shown in U.S. Pat. Nos. 3,462,765 and 3,875,594 to Dr. A. B. Swanson. Another type of prosthesis is of the ball and socket type design, for example that shown in U.S. Pat. No. 4,304,011 issued to Whelan, III.

A further type of prosthesis is formed from two members, one of which is inserted into each of the respective bones in the joint. Alternatively only one side of the joint is replaced with a concavely surfaced implant that articulates against the convex rounded bony structure of the remaining bone in the joint (for example, a metatarsal head). The members of the prosthesis have enlarged heads that are adapted to engage each other or the bone to form a pivotable connection. Examples of such joints are shown in U.S. Pat. Nos. 4,242,759 to White, 4,642,122 to Steffee and 4,231,121 to Lewis, and 4,685,919 to Niwa, et al. The prosthesis of the present invention pertains to the latter type. A problem which has occurred with such implants is that in some cases motion between the concave surface of the implant and the convex surface of the bone becomes limited, such as by soft tissue fibrosis, with the result that motion is lost. The present invention overcomes this problem by providing a one-piece implant having dual articulating means which will assure that bending motion can always be achieved.

Briefly summarized, the present invention provides an improved prosthetic toe joint adapted for replacement of a human toe joint which includes at least one one-piece member for implantation into the bone of the joint. The implant of this invention has a concave articulating surface which articulates against another one-piece component having a mating convex surface or against a mating convex bone surface. This one part component is provided with a flexible hinge section at the junction of its stem and the enlarged head portions. The hinge section is formed from a section of the stem which extends laterally outwardly on both sides of the stem portion adjacent the junction with the head. The laterally enlarged section is provided with a longitudinal channel extending through its midsection to form a hinge. Each of the one-piece components is preferably molded of a flexible elastomeric, physiologically inert material, for example medical grade silicone elastomer of the type marketed by Dow Corning Corporation, Midland, Michigan. One or both of the articular surfaces of the one-piece components may be provided with wear-resistant caps for example a layer of titanium metal which is integral with the articular surface.

Other purposes and objects of the invention will be apparent to persons skilled in the art relating to prostheses of this general type and from a reading of the following specification and inspection of the drawings.

DETAILED DESCRIPTION

Figure 1:
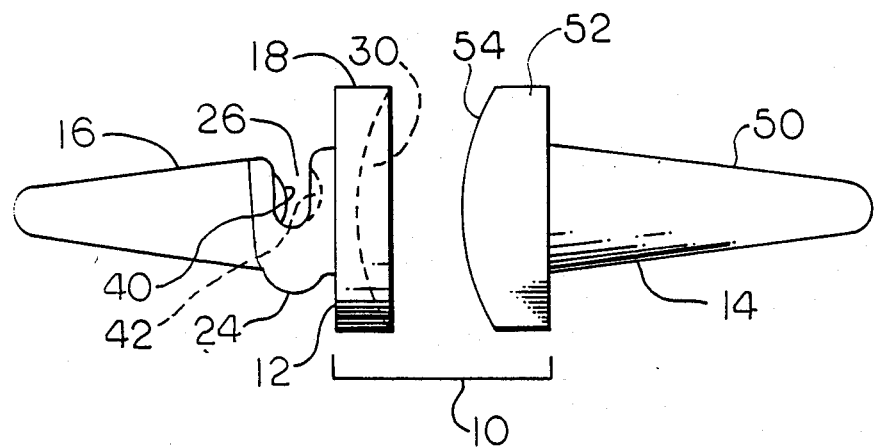
FIG. 1 is a side elevational view showing two one-piece components of a joint prosthesis of the present invention.

Referring to the drawings, in FIG. 1 there is illustrated an implantable joint or prosthesis 10 which is designed for replacement of a human toe joint, generally the joint between the metatarsal and the proximal phalanx. Joint prosthesis 10 is formed of one-piece member 12. Optionally a second, convex member 14 is provided for replacement of the other articulating bone surface of the joint, if necessary.

Figure 2:
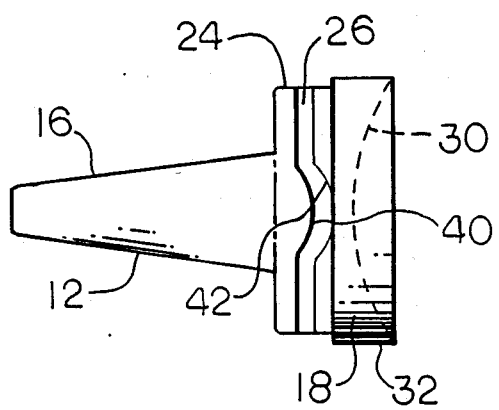
FIG. 2 is a top view of a joint component having a flexible hinge between the stem and the head portions thereof.

As seen in FIGS. 1 and 2, one piece member 12 is provided with an elongated stem portion which is adapted to be inserted into the intramedullary canal of the bone. An enlarged end 18 is provided at the opposite end. One part component 12 is provided with a flexible hinge section 24 at the junction of stem 16 in enlarged head portion 18. The hinged section 24 is formed from a section of stem 16 which extends laterally outwardly on both sides of stem 16. The laterally enlarged section 24 is provided with a longitudinal channel 26 extending through its midsection to form a hinge. In the preferred embodiment the center of channel 26 is provided on one wall with an enlarged central portion 40 and on the opposite wall with a depression 42 which allows projection 40 space for displacement upon flexion of the hinge. Such a thickening and depression has been found to improve flex life of the joint as described in U.S. Pat. No. 3,875,594. Enlarged head portion 18 is provided with a concave articulation surface 30.

As noted herein before, concave surface 30 is adapted to articulate against the convex surface of the bone on the other side of the joint into which it is implanted. The surface of enlarged portion 18 and articulating surface 30 may optionally be provided with a wear-resistant layer 32 formed of titanium or other biologically compatible metal.

If the condition of the convex articular surface of the bone on the opposite side (usually the proximal side) of the joint dictates replacement thereof, a mating, one piece stemmed implant 14 may be provided. One piece component 14 is provided with a stem 50 adapted to fit into the intramedullary canal of the bone on the proximal side of the joint and an enlarged head 52 having a convex articulation surface 54. Surface 54 is provided with a curvature so as to mate and articulate with concave surface 30. In cases where surface 30 is intended to articulate with the bone, its curvature is designed to mate as closely as possible with the shape and curvature of the bone. One piece component 14 may either be formed of metal, ceramic or a hard plastic substance such as polyethylene.

The implants of the present invention are designed primarily to supplement resection arthroplasty of the first metatarsophalangeal joint. The stem of the one piece implant fits into the intramedullary canal of the proximal phalanx with the implant head replacing the base of the proximal phalanx. It thus provides a smooth articulation surface for the first metatarsal head and helps to restore and maintain motion. The hinge section included in the implant of the present invention, it will be seen, provides not only an articulation surface at the location of the natural joint of the toe bone which it replaces, but in cases where motion between the metatarsal head and the concave surface of the implants becomes limited as a result of constrictive soft tissue or the development of irregularities in the metatarsal head with a resultant loss of join motion, the prosthesis of the present invention provides for continued motion in the hinge section thus obviating the necessity of additional surgery.

The preferred material for construction of the one piece implants of this invention is medical grade high performance silicone elastomer. Other biologically compatible elastomers could be substituted. Since the elastomer is softer than bone it is unlikely to cause necrosis or bony resorption. It will also be apprent to those skilled in the art that protective shields of the general type shown in U.S. Pat. No. 4,198,713 or sleeves or grommets of the type described in U.S. Pat. No. 4,158,893 could be used in conjuction with the implants of this invention in order to protect the implant from attrition or laceration by the surface of the bone.

Although particular preferred embodiments of the invention have been disclosed in detail for illustrative purposes, it will be recognized that variations or modifications of the disclosed embodiments lie within the scope of the present invention.

That which is claimed is:

1. An improved prosthetic toe joint adapted for replacement of a human toe joint which includes at least one one-piece member for implantation into the bone of the joint, the implant having a stem and an enlarged head which is provided with a concave articulating surface for articulation against another one-piece component having a mating convex surface or against a mating convex bone surface, the one part component being provided with a flexible hinge section at the junction of its stem and the enlarged head portion, the hinge section being formed from a section of the stem which extends laterally outwardly on both sides of the stem portion adjacent the junction with the head, the laterally enlarged section being provided with a longitudinal channel extending through its midsection to form a hinge, said one-piece component being formed of a flexible elastomeric, physiologically inert material.

2. A prosthesis according to claim 1 wherein said one-piece component is formed of medical grade silicone elastomer.

3. A prosthesis according to claim 1 wherein one wall of said longitudinal channel is thickened near its midsection and the opposite wall is recessed to receive said thickened portion upon flexion of said hinge.

4. A prosthesis according to claim 1 wherein said articulating surface is capped with a layer of biologically compatible metal.

* * * * *